(12) United States Patent
Ameye et al.

(10) Patent No.: US 9,339,464 B2
(45) Date of Patent: May 17, 2016

(54) FAST DISSOLVING AZAPERONE GRANULATE FORMULATION

(75) Inventors: Dieter Bert Leen Ameye, Anzegem (BE); Lieven Van Vooren, Ertvelde (BE); Peter Meerts, Lokeren (BE); Geert Louise F. Van Beeck, Zoersel (BE); Raja Satyanarayana Yekkala, Ghent (BE)

(73) Assignee: Elanco Animal Health Ireland Limited, Indianapolis, IN (US)

( * ) Notice: Subject to any disclaimer, the term of this patent is extended or adjusted under 35 U.S.C. 154(b) by 49 days.

(21) Appl. No.: 14/127,018

(22) PCT Filed: Jun. 21, 2012

(86) PCT No.: PCT/US2012/043499
§ 371 (c)(1),
(2), (4) Date: Dec. 17, 2013

(87) PCT Pub. No.: WO2012/177842
PCT Pub. Date: Dec. 27, 2012

(65) Prior Publication Data
US 2014/0128407 A1    May 8, 2014

(30) Foreign Application Priority Data
Jun. 24, 2011 (EP) ..................................... 11171263

(51) Int. Cl.
| | | |
|---|---|---|
| *A61K 9/16* | (2006.01) |
| *A61K 31/496* | (2006.01) |
| *A61K 9/00* | (2006.01) |
| *A61K 47/12* | (2006.01) |
| *A61K 47/26* | (2006.01) |
| *A61K 47/32* | (2006.01) |
| *A61K 47/36* | (2006.01) |

(52) U.S. Cl.
CPC .................. *A61K 9/16* (2013.01); *A61K 9/0056* (2013.01); *A61K 9/1617* (2013.01); *A61K 9/1623* (2013.01); *A61K 9/1635* (2013.01); *A61K 9/1652* (2013.01); *A61K 31/496* (2013.01); *A61K 47/12* (2013.01); *A61K 47/26* (2013.01); *A61K 47/32* (2013.01); *A61K 47/36* (2013.01)

(58) Field of Classification Search
None
See application file for complete search history.

(56) References Cited

U.S. PATENT DOCUMENTS

2004/0156894 A1* 8/2004 Grother et al. ................ 424/465
2011/0027377 A1* 2/2011 Remon et al. ................ 424/499

FOREIGN PATENT DOCUMENTS

WO    2010/031805 A1    3/2010
WO    2010/031809 A1    3/2010

OTHER PUBLICATIONS

USP Azaperone Safety Data Sheet [online] Retrieved on Aug. 19, 2014 (Issue date: Jun. 2, 2006) url:<http://www.usp.org/pdf/EN/referenceStandards/msds/1045756.pdf>.*
Schoneker.Encyclopedia of Pharmaceutical Technology 2006 (3rd Ed.) chapter 43, pp. 648-670.*
Rowe et al. Handbook of Pharmaceutical Excipients (6th Ed. (2009), pp. 189-196, 326-329, 364-369, 731-732.*
Gonyou et al., "Effects of amperozide and azaperone on aggression and productivity of growing-finishing pigs," J Anim Sci, 1988; 66(11):2862-2863.

* cited by examiner

*Primary Examiner* — Melenie McCormick
*Assistant Examiner* — Taina D Matos Negron
(74) *Attorney, Agent, or Firm* — James J. Sales; Sam J. Barkley

(57) ABSTRACT

The present invention relates to a fast dissolving granulate formulation containing the veterinary drug azaperone and a method for preparing said granulate formulation.

9 Claims, No Drawings

FAST DISSOLVING AZAPERONE GRANULATE FORMULATION

CROSS REFERENCE TO RELATED APPLICATIONS

This application is a U.S. national stage application of Application No. PCT/US2012/043499, filed Dec. 21, 2012, which application claims priority from EP 11171263.4, filed Dec. 24, 2011.

The present invention relates to a fast dissolving granulate formulation containing the veterinary drug azaperone and a method for preparing said granulate formulation.

Azaperone is a butyrophenone neuroleptic discovered in the early 1960s by Janssen Pharmaceutica laboratories and is currently available as the 4% sterile injectable solution called Stresnil. Chemically, it is 4'-fluoro-4-(4-(2-pyridyl)-1-piperazinyl-butyrophenone and has the following structure:

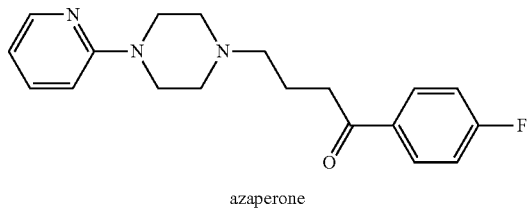 [SMILES: O=C(CCCN1CCN(c2ccccn2)CC1)c1ccc(F)cc1]

azaperone

Stresnil™ (azaperone) injection is indicated for the prevention of aggressiveness and stress by inducing a variable degree of sedation. Following a single dose of Stresnil™, pigs may be mixed and fighting is eliminated or greatly reduced.

WO-2010/031805 discloses a method for improving growth performance in animals without causing sedation by orally administering azaperone in a low dose together with food or drinking water. Improving growth performance comprises the increase of growth rate over a certain period of time.

WO-2010/031809 discloses a method of reducing antibiotic usage in animals by orally administering azaperone in a low dose together with food or drinking water.

Both WO-2010/031805 and WO-2010/031809 disclose the following concentrated water dilutable solution to administer azaperone with drinking water or through a water supply system:

| | |
|---|---|
| Azaperone | 100 mg |
| Citric acid | 80 mg |
| Methyl parahydroxybenzoate | 2 mg |
| Propyl parahydroxybenzoate | 0.2 mg |
| 35 Purified water q.s. | 1 ml |

The preferred administration route for oral administration of azaperone in a low dose continuously provided together with food or drinking water as disclosed in WO 2010/031805 and WO 2010/031809 is administration of azaperone through a water distribution system such as for providing drinking water. Many livestock farms are already equipped with the necessary devices to administer medication via drinking water hence no special modifications are needed to administer azaperone together with drinking water via the water distribution system. The dosing of azaperone can be adjusted in function of the water consumption of the livestock.

Granulate formulations are easier to transport and often have a better shelf life and increased chemical stability of the active ingredient over concentrated liquid formulations. The Committee for Medicinal Products for Veterinary Use (CVMP), a part of the European Medicines Agency, has issued a guideline on "Quality aspects of pharmaceutical veterinary medicines for administration via drinking water" as EMEA/CVMP/540/03 Rev. 1 on 15 Apr. 2005 (see www.ema.europa.eu/docs/en_GB/document_library/Scientific_guideline/2009/10/WC50 0004462.pdf) setting out quality data requirements and includes guidance for in-use stability testing. A major requirement is the requirement for complete dissolution of the veterinary product within 10 minutes in hard and soft water at a temperature in the range of 5 to 20° C.

A fast dissolving granulate formulation has now been developed which dissolves in less than 10 minutes in hard and soft water when tested following the requirements as set out in the Guideline EMEA/CVMP/540/03 Rev. 1 of 15 Apr. 2005. Said fast dissolving formulation comprises
  azaperone,
  an acid selected from tartaric acid or citric acid,
  a filler selected from lactose, lactose monohydrate or mannitol,
  a binder selected from maltodextrin, HPMC or povidone, and
  optionally a coloring agent,
  whereby the ratio azaperone to acid ranges from 1:2 to 1:4 (w/w).

"Tartaric acid" as used in the fast dissolving granulate formulations of the present invention encompasses all known forms of tartaric acid such as L-tartaric acid, D-tartaric acid, mesotartaric acid and the 1:1 mixture of the levo and dextro forms 35 DL-tartaric acid. In practice the naturally occurring form of tartaric acid, L-tartaric acid which is also known as dextrotartaric acid, is used since this is the cheapest form of tartaric acid.

"Citric acid" as used in the formulations of the present invention encompasses anhydrous citric acid and citric acid monohydrate. In practice anhydrous citric acid is used since the fast dissolving granules of the present invention tend to be less sticky when anhydrous citric acid is used instead of citric acid monohydrate.

The suitable fillers for use in the fast dissolving azaperone granules of the present invention are selected from lactose, lactose monohydrate or mannitol. In practice the use of lactose monohydrate as a filler is preferred.

The suitable binders for use in the fast dissolving azaperone granules of the present invention are selected from maltodextrin, HPMC (hydroxypropyl methylcellulose or povidone. In practice the use of HPMC as a binder is preferred. HPMC is commercially available in different grades such as, e.g. HPMC 2910 15 mPa·s. Povidone is commercially available in difference grades such as, e.g. povidone K30.

The fast dissolving azaperone granules of the present invention are intended for administration of azaperone to live stock animals through a water distribution system such as for providing drinking water. The term "live stock animals" refers to any non-human warm-blooded animals in particular those produced for consumption such as poultry (chickens, turkey, ducks, ostrich, emu, quail etc.), and ruminants (goats, sheep, and cattle), pigs and rabbits. The azaperone granules are first dissolved in water to obtain a concentrated stock solution with a pre-dilution target dose between 600 to 1200 mg/L. This concentrated stock solution is than connected to the dosing pump of the water distribution system to obtain a target final dose in the drinking water ranging from 6 to 12 mg/L. In order to obtain a visual difference between the concentrated stock solution and the final dilution in the drinking water a coloring agent is added to the azaperone granules.

The dosing of the coloring agent in the azaperone granules and the type of coloring agent is such that the stock solution has a visible color but the final dilution in the drinking water system is clear. Suitable coloring agents are e.g. Patent Blue V (E131), Indigotine (E132, also known as FD&C Blue No. 2), or Brilliant Blue FCF (E133, also known as FD&C Blue No. 1).

The amounts of azaperone, acid, filler, binder and optional coloring agent are selected in such a way so as to obtain the required dissolution within 10 minutes as set out in the Guideline EMEA/CVMP/540/03 Rev. 1 of 15 Apr. 2005. Furthermore the ratio azaperone to acid has to range from 1:2 to 1:4 (w/w) to obtain fast dissolution in the defined pre-concentrate solutions.

Suitable fast dissolving azaperone granulate formulations comprise:
- azaperone in an amount from 5 to 15% (w/w),
- an acid selected from tartaric acid or citric acid in an amount from 10 to 60% (w/w), whereby the ratio azaperone to acid ranges from 1:2 to 1:4 (w/w),
- a binder selected from maltodextrin, HPMC or povidone in an amount from 0.5 to 5%, and
- optionally a coloring agent in an amount from 0.01% to 0.10% (w/w); and
- a filler selected from lactose, lactose monohydrate or mannitol in an amount to make up to 100% (w/w).

The amount of azaperone in the fast dissolving granulate formulations of the present invention ranges from 5 to 15% (w/w). A practical amount is 10% (w/w).

The amount of acid used in the fast dissolving granulate formulations is such that the ratio azaperone to acid ranges from 1:2 to 1:4 (w/w). Based on the amount of azaperone, this means that the amount of acid ranges from 10 to 60% (w/w).

In an embodiment the ratio between azaperone and citric acid in the fast dissolving granulate formulations is 1:3. In another embodiment the ratio between azaperone and tartaric acid is 1:2.

The fast dissolving azaperone granulate formulations are prepared by mixing the binder with water until a homogeneous solution is obtained, followed by adding the optional coloring agent, and spraying this solution on a powder mixture of azaperone, acid and filler in a suitable fluid-bed granulator. After spraying the wet granulates are dried while fluidising and the dried granulates are sieved and collected in a suitable blender and mixed until homogenous. The granulates are then filled into a suitable container.

The fast dissolving azaperone granulate formulations can also be prepared using a high shear wet granulation technique: a mixture of azaperone, acid and filler is mixed by dry blending in a high shear granulator, following by dropwise addition of an aqueous solution comprising the binder and optional coloring agent, and further mixing in the high shear granulator until the desired granules are obtained. These granules are then dried and sieved.

EXAMPLES

1) Formulations

| Composition of formulation 1: | |
| --- | --- |
| Azaperone | 5% (w/w) |
| Citric acid monohydrate | 15% (w/w) |
| Lactose monohydrate | 79.4% (w/w) |
| Maltodextrin | 0.6% (w/w) |

| Composition of formulation 2: | |
| --- | --- |
| Azaperone | 10% (w/w) |
| Citric acid monohydrate | 30% (w/w) |
| Lactose monohydrate | 59.4% (w/w) |
| Povidone K30 | 0.6% (w/w) |

| Composition of formulation 3: | |
| --- | --- |
| Azaperone | 5% (w/w) |
| Citric acid monohydrate | 15% (w/w) |
| Mannitol | 79.5% (w/w) |
| Maltodextrin | 0.5% (w/w) |

| Composition of formulation 4: | |
| --- | --- |
| Azaperone | 10% (w/w) |
| Citric acid anhydrous | 20% (w/w) |
| Lactose monohydrate | 69.5% (w/w) |
| Maltodextrin | 0.5% (w/w) |

| Composition of formulation 5: | |
| --- | --- |
| Azaperone | 10% (w/w) |
| Citric acid anhydrous | 30% (w/w) |
| Lactose monohydrate | 59.3% (w/w) |
| Maltodextrin | 0.65% (w/w) |
| Brilliant Blue (133) | 0.05% (w/w) |

| Composition of formulation 6: | |
| --- | --- |
| Azaperone | 10% (w/w) |
| Tartaric acid | 20% (w/w) |
| Lactose monohydrate | 68.95% (w/w) |
| HPMC 2910 15 mPa · s | 1% (w/w) |
| Brilliant Blue (133) | 0.05% (w/w) |

1) Preparation of Soft/Hard Water

The following two qualities of water were used in the dissolution studies:
- soft water/low pH with a pH range from 5.0 to 7.0 and 60 mg/L or less of calcium carbonate
- hard water/high pH with a pH range from 8.0 to 9.0 and 180 to 350 mg/L of calcium carbonate.

Preparation of both the soft water and the hard water was done in accordance with the guidelines issued by the CVMP in EMEA/CVMP/540/03 Rev. 1 issued on 15 Apr. 2005.

4) Dissolution Testing

The dissolution test is performed as follows: 3 g of azaperone granules are transferred into an empty beaker of 1 L. A quantity (i.e. 500 mL) of soft or hard water is added to reach a concentration of 600 mg/L of azaperone (this is the pre-dilution concentration). The content of the beaker is stirred manually using a glass rod at approximately 60 rpm until complete dissolution of the granules is visually observed.

Dissolution of all formulations as described in part 1 was seen within 5 minutes in either soft or hard water. The pH of the dissolution medium after complete dissolution was between 3.1 and 3.6.

The invention claimed is:

1. A fast dissolving granulate formulation comprising azaperone, an acid selected from tartaric acid or citric acid, a filler selected from lactose, lactose monohydrate, or mannitol, a binder selected from maltodextrin, hydroxylpropyl methylcellulose, or povidone, and optionally a coloring agent; whereby the ratio of azaperone:acid is between about 1:2 to about 1:4 (w/w) and wherein complete dissolution of the granulate formulation occurs within 5 minutes when the formulation is added to water.

2. The formulation of claim 1 wherein the acid is tartaric acid.

3. The formulation of claim 1 wherein the filler is lactose monohydrate.

4. The formulation of claim 1 wherein the binder is HPMC.

5. The formulation of claim 1 comprising azaperone in an amount from about 5 to about 15% (w/w), an acid selected from tartaric acid or citric acid in an amount from about 10 to about 60% (w/w), a binder selected from maltodextrin, hydroxylpropyl methylcellulose, or povidone in an amount from about 0.5 to about 5%, optionally a coloring agent in an amount from about 0.01% to about 0.10% (w/w); and a filler selected from lactose, lactose monohydrate, or mannitol in an amount to make up to 100% (w/w); whereby the ratio of azaperone:acid is between about 1:2 to about 1:4 (w/w).

6. The formulation of claim 5 comprising azaperone at about 10% (w/w), tartaric acid at about 20% (w/w), lactose monohydrate at about 69% (w/w), hydroxylpropyl methylcellulose at about 1% (w/w), and Brilliant Blue at about 0.05% (w/w).

7. A method of administering the formulation of claim 1 to an animal, wherein the administration is via a water distribution system.

8. A method of improving growth performance in an animal comprising administering to the animal in need thereof a therapeutically effective amount of the formulation of claim 1.

9. A method of reducing antibiotic usage in an animal comprising administering to the animal in need thereof a therapeutically effective amount of the formulation of claim 1.

* * * * *